US005482753A

United States Patent [19]

Langan et al.

[11] Patent Number: 5,482,753

[45] Date of Patent: Jan. 9, 1996

[54] FORM/LABEL COMBINATION

[75] Inventors: Joseph Langan, Cheektowaga; Khaled Khatib, Youngstown, both of N.Y.

[73] Assignee: Moore Business Forms, Inc., Grand Island, N.Y.

[21] Appl. No.: 65,782

[22] Filed: May 24, 1993

[51] Int. Cl.[6] .................... A61F 13/02

[52] U.S. Cl. .................... 428/42; 281/2; 281/5; 283/101; 283/105; 283/107; 283/108; 428/43; 428/174; 428/187; 428/195; 428/481; 428/537.5

[58] Field of Search .................... 428/40, 41, 42, 428/43, 131, 137, 195, 174, 187, 195, 481, 537.5; 156/204, 227, 260; 283/56, 81, 101, 105, 107, 108; 281/2, 5

[56] References Cited

U.S. PATENT DOCUMENTS

| | | | |
|---|---|---|---|
| 3,226,862 | 1/1966 | Gabruk | 40/2 |
| 3,820,261 | 6/1974 | Beall, Jr. | 40/2 |
| 4,211,434 | 7/1980 | Reese | 282/11.5 |
| 4,910,058 | 3/1990 | Jameson | 428/42 |
| 4,932,684 | 6/1990 | Vermeulen | 283/81 |
| 4,938,507 | 7/1990 | Ashby et al. | 282/9 R |
| 4,983,438 | 1/1991 | Jameson | 428/42 |
| 5,129,682 | 7/1992 | Ashby | 283/81 |
| 5,178,419 | 1/1993 | Bolnick et al. | 283/81 |
| 5,209,698 | 5/1993 | Dolan | 462/17 |
| 5,316,344 | 5/1994 | Popat et al. | 283/81 |
| 5,324,559 | 6/1994 | Brombacher | 428/40 |
| 5,348,780 | 9/1994 | Bogg et al. | 428/42 |
| 5,351,426 | 10/1994 | Voy et al. | 40/638 |

*Primary Examiner*—Patrick J. Ryan
*Assistant Examiner*—William A. Krynski
*Attorney, Agent, or Firm*—Nixon & Vanderhye

[57] ABSTRACT

A business form is particularly useful to provide labels applied to appliances, as well as appliance registration information on a paper substrate associated with the labels. A common substrate mounts a repositional adhesive label and a permanent (piggyback) adhesive label while at the same time providing appliance registration information. The substrate and the labels may be variable imaged at the same time, as with a common appliance ID number. The removable adhesive label preferably has indicia indicating appliance energy costs, while the permanent adhesive label (of paper, plastic film or metal foil) takes the place of a typically metal appliance ID tag. A release material is preferably spot coated on the top surface of the substrate, and the repositional adhesive label is applied over the release material spot coat.

20 Claims, 4 Drawing Sheets

Fig. 3
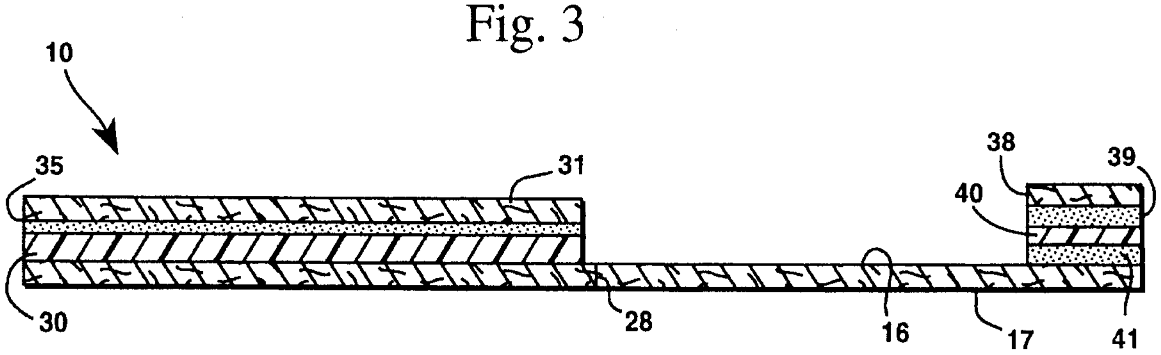
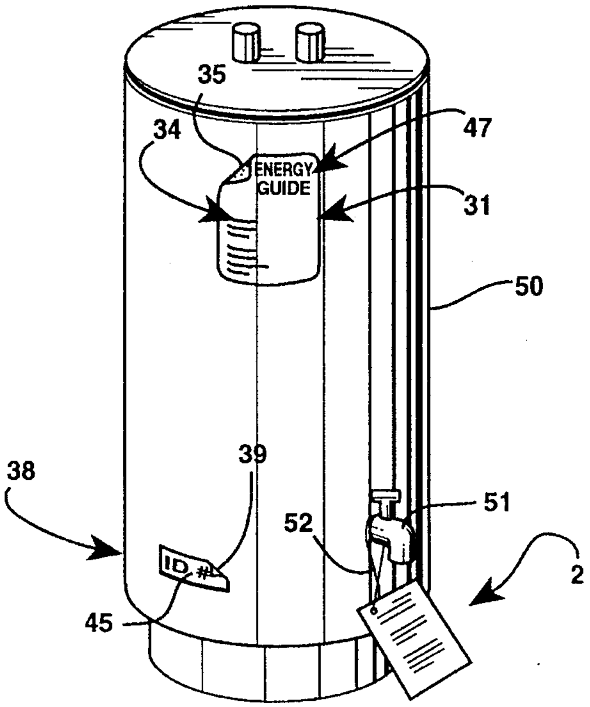
Fig. 4

FORM/LABEL COMBINATION

BACKGROUND AND SKY OF THE INVENTION

The vast majority of commercially marketed new electrical appliances are subject to product registration for warranty and other purposes. Also, it is desirable to provide a unique identification number on the appliance, and for most appliances it is also desirable or necessary (to conform to national law) to provide information about the appliance directly on the appliance, including energy cost information. According to the present invention, all of these needs are accomplished utilizing a particular single business form, and the individual label components of the business form also are advantageous per se.

According to the present invention, on the same business form is provided product (e.g. appliance) registration information (such as for warranty purposes), an informational label (typically appliance energy cost information), and an identification label. The labels and the product registration information are associated together on the same form which is adapted to be imaged by an impact or non-impact printer with variable information, such as the identification number of the appliance, providing a much simplified procedure for the appliance manufacturer or shipper, while at the same providing advantages to the ultimate consumer. According to the present invention the label providing appliance information (such as energy cost information) has repositional adhesive so that when it is applied to an appliance it can be readily removed by the ultimate consumer without the need for scraping (which may cause damage to the appliance finish), and without leaving unsightly residues.

The business form of the invention also includes a permanent adhesive label which is adapted to take the place of the metal ID plates commonly provided on appliances. Metal ID plates may scrape floors or walls during installation, are relatively expensive, and require significant time to affix to the appliance. The permanent adhesive labels according to the invention, however, have UL, AGA and CSA approval for electronic appliances and components, and may be made of durable paper, plastic film, or metal foil. Since all the components of the business form may be variably imaged with the same information (e.g. an appliance ID number) and then readily removed from (e.g. either peeled off or detached from by perforations) the paper substrate forming the business form, they significantly simplify procedures for appliance manufacturers or shippers.

According to one aspect of the present invention, a business form is provided comprising the following elements: A paper substrate having top and bottom surfaces. Static printing on the top surface. A release material spot coating on the top surface, covering a first portion of the top surface of a size significantly less than the entire top surface. A removable label with repositional adhesive applied over the release material spot coating, with the repositional adhesive of the removable label contacting the spot coating. And a permanent piggyback label with permanent adhesive applied to a second portion of the top surface, spaced from the first portion.

The removable label may cover part of the static printing, which is exposed when the removable label is removed. Perforation lines may be provided in the substrate bordering the static printing. The static printing preferably comprises appliance registration information (e.g. for warranty purposes), and a common ID number is preferably provided on all of the paper substrate, removable label, and permanent label. The removable label preferably has appliance energy usage information imaged thereon, while the permanent label is of durable paper, plastic film, or metal foil, and has an appliance number ID number imaged thereon. The release material preferably is a silicone coating, and the static printing is preferably provided on both the top and bottom surfaces.

According to another aspect of the present invention a business form is provided comprising the following elements: A paper substrate having top and bottom surfaces. Static printing on the top surface. A release material spot coating on the top surface, covering a first portion of the top surface of a size significantly less than the entire top surface. A removable label with repositional adhesive applied over the release material spot coating, with the repositional adhesive of the removable label contacting the spot coating. And a permanent label having permanent adhesive, the permanent adhesive adhered to the substrate, spaced from the removable label, in a manner that allows ready removal of the permanent label.

According to yet another aspect of the present invention a method of applying information to and with an electrical appliance, using a paper substrate, is provided. The method comprises the steps of: (a) Printing appliance registration information on the paper substrate. (b) Applying a repositional adhesive label on the paper substrate. (c) Applying a permanent adhesive label on the paper substrate spaced from the repositional adhesive label. (d) Variably imaging information on the paper substrate, repositional adhesive label, and permanent adhesive label. (e) Removing the repositional and permanent adhesive labels from the substrate and applying them to the electrical appliance. And (f) detaching the appliance registration information from the rest of the substrate, and associating the appliance registration information with the appliance.

The method according to the invention also preferably comprises the further step, between steps (a) and (b), of applying a release material coat to a first portion of the substrate, and step (b) is practiced to apply the repositional adhesive label over that first portion. Step (c) is preferably practiced by blowing on a piggyback label. Step (d) is preferably practiced, with a non-impact or impact printer to variably image a common ID number on the paper substrate, repositional adhesive label, and permanent adhesive label.

The paper substrate is preferably provided with perforations, and step (f) is practiced to detach the appliance registration information from the rest of the substrate along the perforations, and to put it in the same packaging as the appliance (either entirely separate from the appliance, or connected to the appliance with a string, tape, or the like). Also, either there is the further step prior to step (b), or step (d) is practiced, so as to print energy cost information on the repositional adhesive label.

It is a primary object of the present invention to provide an effective business form, and method of applying information to and with an electrical appliance, that greatly facilitate associating information with an appliance. This and other objects of the invention will become clear from an inspection of the detailed description of the invention, and from the appended claims.

BRIEF DESCRIPTION OF THE DRAWINGS

FIG. 3 is a cross-sectional view of the business form of FIG. 1 taken along lines 3—3 thereof;

FIG. 4 illustrates the labels from the business form of FIGS. 1 through 3 attached to an electrical appliance (hot water heater) and the product registration information associated with the appliance.

DETAILED DESCRIPTION OF THE DRAWINGS

Figure 1:
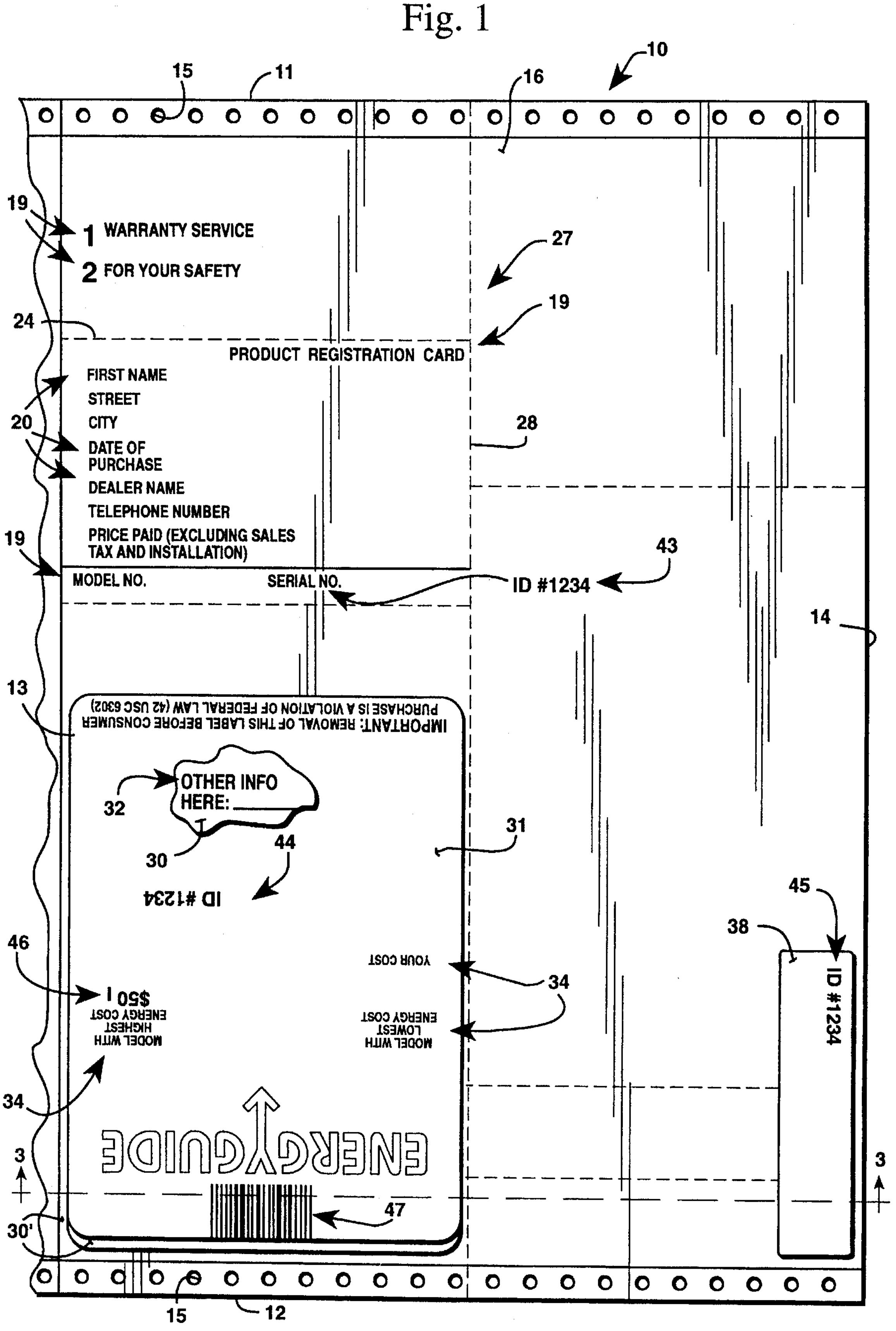
FIG. 1 is a top plan view of a top surface of an exemplary embodiment of a business form according to the invention.
Figure 2:
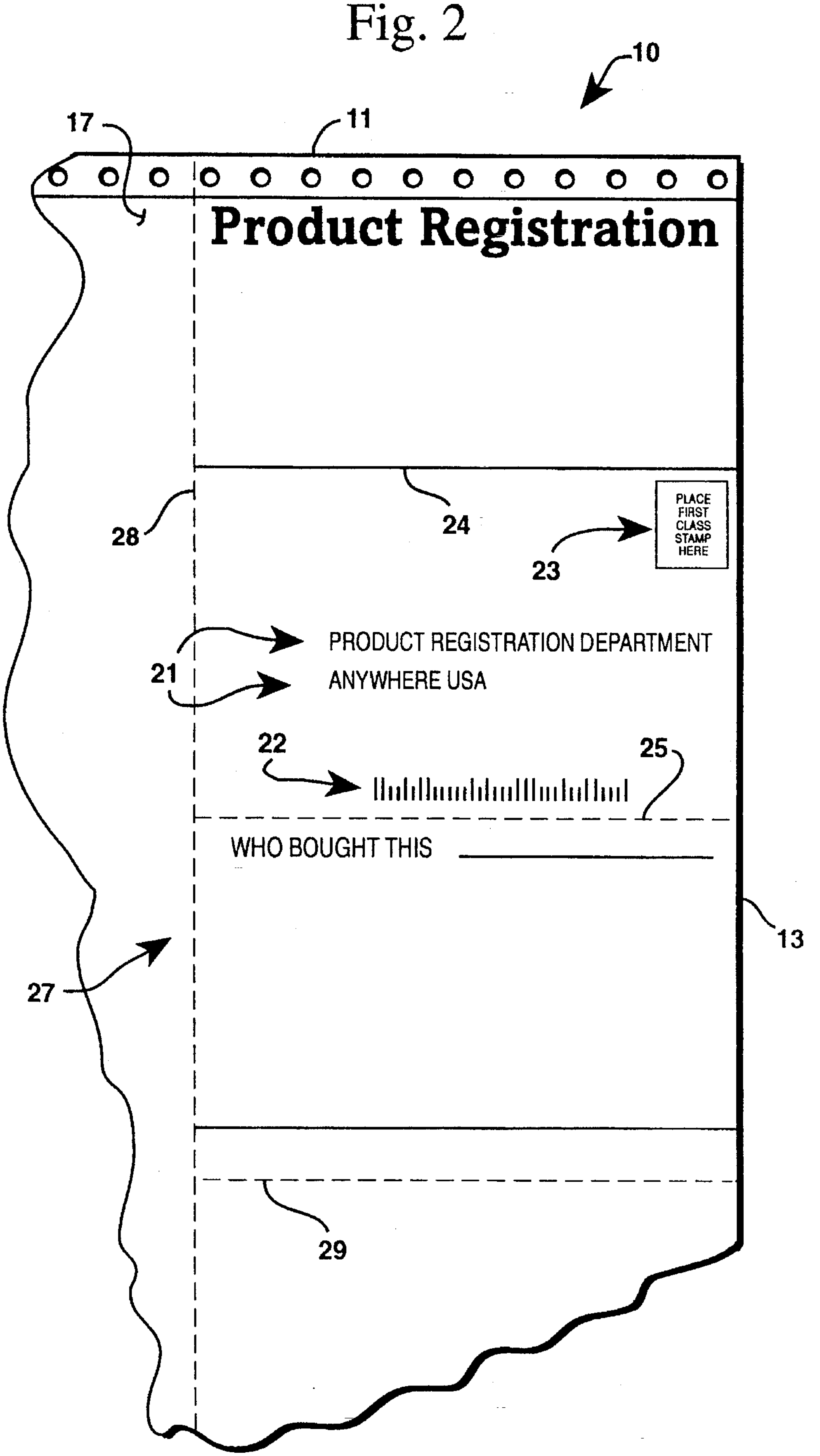
FIG. 2 is a detailed view of part of the bottom surface of the business form of FIG. 1.

An exemplary business form according to the present invention is shown generally by reference numeral 10 in FIGS. 1 and 2. In FIG. 1 the business form is shown in continuous format, having side edges 11 and 12, and end edges 13, 14, the end edge 13 being indicated as a perforation line connecting the business form 10 to a like business form in continuous format. Tractor drive openings 15 are disposed along both of the side edges 11, 12 for facilitating feeding of the form 10 through a printer.

The form 10 preferably comprises a paper substrate, of relatively heavy weight, e.g. the typical weight of a postcard. A substrate forming the business form 10 has a top surface 16 (FIG. 1), and a bottom surface 17.

Printed on the top surface 16 (preferably static printed as on a Flexopress) is various indicia relating to appliance registration information. This indicia preferably includes information to the ultimate purchaser of an appliance with which the product registration information is associated, such as the indicia 19 illustrated in FIG. 1, as well as blank spaces for the ultimate purchaser to fill in his/her name, address, date of purchase, and other information useful or necessary for product registration, consumer surveys, etc., such as shown generally by indicia 20 in FIG. 1.

Other static printing is also preferably provided on the bottom surface 17 of the business form 10 paper substrate, as illustrated in FIG. 2. This information on the bottom surface 17 preferably includes reply address indicia 21, including bar coding 22, and indicia indicating a place for postage 23, to facilitate mailing of the appliance registration information back to the manufacturer or shipper. Preferably fold lines 24, 25 are provided to facilitate folding of the entire product registration card 27 (see FIGS. 1, 2 and 4) into a mailable form the size of a postcard. The element 27 is connected to the rest of the paper substrate of the form 10 by perforation lines 28, 29 at the borders thereof so that it may be readily detached from the rest of the form 10 when desired.

The form 10 preferably also comprises a release material coating, such as a silicone coating, on a first portion of the top surface 16 of the substrate forming the form 10, the first portion having a size much less than the entire top surface 16 of the form 10. The silicone coating is indicated by reference numeral 30 in FIGS. 1 and 3 and typically has substantially the same dimensions as the removable label 31 which is applied to the surface 16 over the release coat 30, the release coat 30 just slightly overlapping the removable label 31, as indicated by the portions 30' of the release coating 30 seen in FIG. 1. Note that—in order to conserve space—it may be desirable or appropriate for the label 31 to cover some of the static indicia printed on the top surface 16, as illustrated for the indicia 32 in FIG. 1.

The label 31 is preferably of paper or plastic film and has a top surface (visible in FIG. 1) having various indicia thereon. The indicia may include, for example, energy cost indicia 34 which may be either static printed on the label 31 before it is applied to the business form 10, and/or variably printed on the label 31 after it is applied to the form 10. On the back surface of the label 31, as seen in FIGS. 3 and 4, is a coating 35 of repositional adhesive. The repositional adhesive can be of any conventional type, such as CLEAN-TAC® adhesive available from Moore Business Forms, Inc. of Lake Forest, Ill., or that commonly used with the NOTE STIX® and POST-IT® products readily available on the market. While the repositional adhesive 35 is such that it would release from the top surface 16 of the paper substrate forming the form 10 in any event, the release coating 30 insures ready peelability so that the possibility of ripping the label 31, or destroying any underlying indicia 32 on the surface 16, is avoided.

Also provided as part of the business form 10, preferably associated with the top surface 16, is a permanent label 38. The permanent label 38 may be of a durable paper, plastic film, or metal foil, and on the back surface thereof (see FIGS. 3 and 4) it has permanent adhesive 39. The permanent label 38, and adhesive 39 thereof, are adhered to the surface 16, spaced from the removable label 31, in a manner that allows ready removal thereof from the surface 16. In the preferred embodiment illustrated in the drawings, this is accomplished by providing the label 38 with a piggyback construction. That is, the adhesive 39 thereof engages a release sheet 40, which is connected to the top surface 16 of the form 10 by permanent adhesive 41 (see FIG. 3). The adhesive 39 will not permanently adhere to the release sheet 40 so that the label 38 may be readily removed therefrom.

The business form 10 is designed to be variably imaged with an impact or non-impact printer in a simple and effective manner. For example, the form 10 may be driven, facilitated by tractor drive openings 15, through a printer and any desired variable information applied, preferably only to the top surface 16, but if necessary a duplex printer can be utilized to also apply variable indicia to the bottom surface 17. Typical indicia that is applied by variable imaging comprises a unique identification number for an appliance with which the product registration information card 27, removable label 31, and permanent label 38 will be associated. This identification number indicia is illustrated in FIG. 1 by reference numerals 43, 44, and 45. The indicia 43 is provided on the top surface 16 of the product registration card 27, the indicia 44 on the removable label 31, and the indicia 45 on the permanent label 38. Of course, a wide variety of other indicia may also be variably imaged, such as actual dollar amounts associated with the indicia 34 (see indicia 46 in FIG. 1), and/or a conventional product bar code FIG. 4 illustrates the various components of the business form 10 associated with an electrical appliance, in this case an electrical hot water heater 50. The removable label 31, with the energy cost and like indicia 34, 47, thereon, is applied to a readily visible part of the heater 50, and the permanent label 38 is also applied to the heater 50, although it need not be applied at a readily visible part. The product registration information card 27 may be packed in the same package as the water heater 50, or may be applied thereto by a piece of tape or—as illustrated in FIG. 4—may be connected to a part of the appliance 50 (e.g. drain spout 51) with string 52

Figure 5:
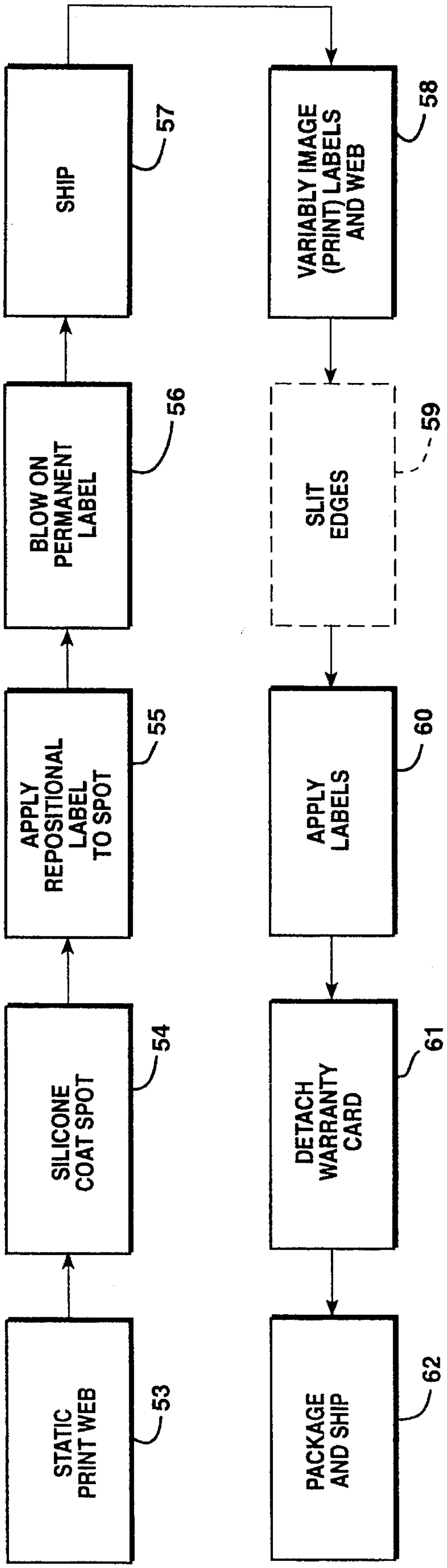
FIG. 5 is a schematic block diagram illustrating an exemplary method according to the present invention.

FIG. 5 schematically illustrates an exemplary method of creating and applying information to and with an electrical appliance (such as the hot water heater 50). First, a paper web, which forms the form 10, is static printed as indicated by box 53, e.g. on a Flexopress. Then the silicone coating 30 is spot coated on a portion of the web top surface 16, as indicated by box 54. Then the repositional adhesive label 31 is applied to the silicone spot coat 30, as indicated by box 55. The label 31 may be provided in a linerless roll configuration, or a linerless cut sheet configuration, or on a liner, and after being removed from the roll, liner, or the like the adhesive 35 of the label 31 engages the coating 30. The label 38 is preferably blown on the surface 16 in piggyback configuration (see FIG. 3) using conventional blow-on equipment, as indicated by box 56. All of these steps preferably are performed at the location of the business forms manufacturer and then the business form 10 (without any variable imaging and still in continuous form) is shipped to the location of the appliance manufacturer or shipper, as schematically illustrated by box 57 in FIG. 5(the shipping step is by no means essential; rather all activities can be performed at the same site).

At the appliance manufacturer's or shipper's facility, the form 10 is passed through an impact or non-impact printer where the variable indicia (e.g. 43–47) is imaged on the top surface 16 of the product registration card 27, and on the top faces of the labels 31, 38, as indicated by box 58 in FIG. 5. If desired, the tractor drive openings 15 of the form 10 may be slit off by conventional slitting equipment, as illustrated schematically by dotted line box 59 in FIG. 5, but in any event, the labels 31, 38 are peeled from the release coat 30 and release sheet 40, respectively, and applied to the appliance 50, as indicated by box 60 in FIG. 5. The product registration information card 27 is then detached from the rest of the form 10 along the perforation lines 27, 29 (and along perforation line/edge 13 if not previously detached) as indicated by box 61, and then the product registration card 27 is packaged with the appliance 50 (as indicated by attachment via string 52 in FIG. 4) and then shipped to the consumer or retail establishment, as indicated by box 62 in FIG. 5. There may be a wide variety of changes to the sequence of the steps illustrated in FIG. 5; for example, the permanent label 38 may be blown onto the substrate 16 at the same time as, or prior to, the positioning of the label 31 thereon, and under some circumstances the release coating 30 can be made wider so that the label 38 can be blown on directly onto the release coating 30, rather than in the piggyback fashion.

It will thus be seen that according to the present invention a business form and method are provided which greatly facilitate the application of labels to, and association of product registration information with, electrical appliances or the like. While the invention has been herein shown and described in what is presently conceived to be the most practical and preferred embodiment, it will be apparent to those of ordinary skill in the art that many modifications may be made thereof within the scope of the invention,, which scope is to be accorded the broadest interpretation of the appended claims so as to encompass all equivalent products and processes.

What is claimed is:

1. A business form comprising:

a paper substrate having top and bottom surfaces;

static printing on said top surface;

a release material spot coating on said top surface, covering a first portion of said top surface of a size less than the entire top surface;

a removable label with repositional adhesive applied over said release material spot coating, with the repositional adhesive of said removable label contacting said spot coating; and a permanent piggyback label with permanent adhesive applied to a second portion of said top surface, adjacent but spaced from said first portion.

2. A business form as recited in claim 1 wherein said removable label and release material spot coating cover part of said static printing.

3. A business form as recited in claim 2 wherein said removable label has indicia thereon relating to energy usage of an appliance.

4. A business form as recited in claim 1 further comprising perforation lines formed in said paper substrate bordering and static printing and between said first and second portions.

5. A business form as recited in claim 4 wherein said static printing comprises appliance registration information.

6. A business form as recited in claim 5 further comprising common appliance identification indicia on said paper substrate top surface, said removable label, and said permanent label.

7. A business form as recited in claim 1 wherein said permanent label is made of a material that will be durable and resist wear once side label is applied to an appliance, and is a material selected from the group consisting essentially of durable paper, plastic film, and metal foil; and further comprising an appliance identification number imaged on said permanent label.

8. A business form as recited in claim 7 wherein said removable label has indicia thereon relating to energy usage of an appliance.

9. A business form as recited in claim 1 wherein said removable label has indicia thereon relating to energy usage of an appliance.

10. A business form as recited in claim 1 wherein static printing is also provided on the bottom surface of said paper substrate.

11. A business form as recited in claim 1 wherein said release material spot coating comprises a silicone coating.

12. A business form as recited in claim 1 wherein said static printing comprises appliance registration information.

13. A business form as recited in claim 12 further comprising common appliance identification indication on said paper substrate top surface, said removable label, and said permanent label.

14. A business form comprising:

a paper substrate having top and bottom surfaces;

static printing on said top surface;

a release material spot coating on said top surface, covering a first portion of said top surface of a size less than the entire top surface;

a removable label with repositional adhesive applied over said release material spot coating, with the repositional adhesive of said removable label contacting said spot coating; and a permanent label having permanent adhesive, said permanent adhesive adhered to said substrate, adjacent but spaced from said removable label, in a manner that allows ready removal of said permanent label.

15. A business form as recited in claim 14 wherein said permanent label is adhered to the substrate in a manner that allows ready removal of the permanent label by a release material adhered to one of said top and bottom surfaces of said paper substrate.

16. A business form as recited in claim 14 wherein static printing is also provided on the bottom surface of said paper substrate.

17. A business form as recited in claim 14 wherein said release material spot coating comprises a silicone coating.

18. A business form as recited in claim 14 wherein said removable label has indicia thereon relating to energy usage of an appliance.

19. A business form as recited in claim 14 wherein said static printing comprises appliance registration information.

20. A business form as recited in claim 14 wherein said permanent label is made of a material that will be durable and resist wear once said label is applied to an appliance, and is a material selected from the group consisting essentially of durable paper, plastic film, and metal foil; and further comprising an appliance identification number imaged on said permanent label.

* * * * *